United States Patent
Dunkley et al.

(10) Patent No.: US 11,498,880 B2
(45) Date of Patent: *Nov. 15, 2022

(54) CALCIUM PHOSPHATE GRANULES AND METHODS OF MAKING THEM

(71) Applicant: Warsaw Orthopedic, Inc., Warsaw, IN (US)

(72) Inventors: Ian Dunkley, Memphis, TN (US); Gretchen Selders, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/523,204

(22) Filed: Jul. 26, 2019

(65) Prior Publication Data

US 2021/0024430 A1    Jan. 28, 2021

(51) Int. Cl.
| | | |
|---|---|---|
| *C04B 38/00* | (2006.01) | |
| *C04B 38/06* | (2006.01) | |
| *C04B 35/447* | (2006.01) | |
| *A61L 27/12* | (2006.01) | |
| *A61L 27/56* | (2006.01) | |

(52) U.S. Cl.
CPC ............ *C04B 38/009* (2013.01); *A61L 27/12* (2013.01); *A61L 27/56* (2013.01); *C04B 35/447* (2013.01); *C04B 38/0054* (2013.01); *C04B 38/067* (2013.01); *A61L 2400/08* (2013.01); *A61L 2430/02* (2013.01); *C04B 2235/447* (2013.01)

(58) Field of Classification Search
CPC .......... C01B 25/35; C04B 38/00; A61K 33/42
USPC .............................. 423/308; 424/423; 501/81
See application file for complete search history.

(56) References Cited

U.S. PATENT DOCUMENTS

| | | | |
|---|---|---|---|
| 4,752,457 A * | 6/1988 | Toriyama | ............ C01B 25/325 423/308 |
| 5,352,715 A | 10/1994 | Wallace et al. | |
| 6,316,091 B1 | 11/2001 | Richart et al. | |
| 7,842,300 B2 | 11/2010 | Atkinson et al. | |
| 8,431,147 B2 | 4/2013 | Drapeau et al. | |
| 8,486,080 B2 | 7/2013 | McKay | |
| 8,653,029 B2 | 2/2014 | Vickers et al. | |
| 8,926,552 B2 | 1/2015 | Walsh | |
| 8,926,710 B2 | 1/2015 | McKay | |
| 9,056,150 B2 | 1/2015 | Gross et al. | |
| 8,968,323 B2 | 3/2015 | McKay | |
| 9,034,358 B2 | 5/2015 | Behnam et al. | |
| 2002/0062154 A1 * | 5/2002 | Ayers | ...................... A61L 27/56 623/23.76 |
| 2003/0049328 A1 | 3/2003 | Dalal et al. | |
| 2005/0163820 A1 | 7/2005 | Fischer | |
| 2005/0186240 A1 | 8/2005 | Ringeisen et al. | |
| 2008/0031914 A1 | 2/2008 | Drapeau et al. | |
| 2008/0147065 A1 | 6/2008 | McKay et al. | |
| 2010/0112330 A1 | 5/2010 | Kuwayama et al. | |
| 2011/0276147 A1 | 11/2011 | Cook et al. | |
| 2012/0107383 A1 | 5/2012 | McKay | |
| 2014/0294971 A1 | 10/2014 | Olympus et al. | |
| 2015/0024023 A1 | 1/2015 | Gibson et al. | |
| 2017/0151371 A1 | 6/2017 | Engqvist et al. | |

FOREIGN PATENT DOCUMENTS

| | | |
|---|---|---|
| CN | 1513806 A | 7/2004 |
| CN | 1621391 A | 6/2005 |
| CN | 1951866 A | 4/2007 |
| CN | 101432030 A | 5/2009 |
| CN | 103467104 A | 12/2013 |
| CN | 103585677 A | 2/2014 |
| CN | 104119072 A | 10/2014 |
| CN | 108079374 A | 5/2018 |
| CN | 108114316 A | 6/2018 |
| CN | 108601864 A | 9/2018 |
| DE | 102005040848 A1 | 3/2007 |
| EP | 1727489 B1 | 8/2016 |
| JP | 2006198276 A | 8/2006 |
| WO | 2017/075613 A1 | 5/2017 |

OTHER PUBLICATIONS

Daculsi et al., "The micro macroporous biphasic calcium phosphate concept for bone reconstruction and tissue engineering." Biomaterials: Fundamentals, Processing: 2008; pp. 1-44. (Year: 2008).*

(Continued)

*Primary Examiner* — Walter E Webb
(74) *Attorney, Agent, or Firm* — Sorell, Lenna & Schmidt, LLP; William D. Schmidt, Esq.

(57) ABSTRACT

A method of making porous ceramic granules is provided. The method comprises heating pore-forming agent particles to a temperature above a glass transition temperature for the pore-forming agent particles; contacting the heated pore-forming agent particles with a ceramic material to form a mixture of pore-forming agent particles and ceramic material; heating the mixture to remove the pore-forming agent particles from the mixture to form a porous ceramic material; and micronizing the porous ceramic material to obtain the porous ceramic granules, wherein the porous ceramic granules have an average diameter from about 50 μm to 800 μm. The porous ceramic granules are also disclosed.

18 Claims, 10 Drawing Sheets

(56) References Cited

OTHER PUBLICATIONS

Mohammadi et al., "Fabrication of dense and porous biphasic calcium phosphates: Effect of dispersion on sinterability and microstructural development." International Journal of Applied Ceramic Technology 2019;16:1797-1806. First published Jan. 24, 2019 (Year: 2019).*

International Search Report and Written Opinion dated Nov. 5, 2020, issued by the International Searching Authority (ISA/KR) in International Application No. PCT/US2020/042804 filed Jul. 20, 2020.

Office Action issued by the Chinese National Intellectual Property Administration dated Jul. 7, 2022 in corresponding Chinese Patent Application No. 202080049742.7 (Warsaw Orthopedic, Inc.).

Office Action issued by the Chinese National Intellectual Property Administration dated Jul. 28, 2022 in Chinese Patent Application No. 202080049697.5 (Warsaw Orthopedic, Inc.).

Office Action issued by the Chinese National Intellectual Property Administration dated Aug. 29, 2022 in Chinese Patent Application No. 202080049730.4 (Warsaw Orthopedic, Inc.).

* cited by examiner

CALCIUM PHOSPHATE GRANULES AND METHODS OF MAKING THEM

BACKGROUND

Bone defects may be caused by a number of different factors, including but not limited to trauma, pathological disease or surgical intervention. Because bone provides both stability and protection to an organism, these bone defects can be problematic. In order to address these defects, compositions that contain both natural and synthetic bone materials have been developed. These compositions may, depending upon the materials contained within them, be used to repair tissues and to impart desirable biological and/or mechanical properties.

Among the known bone repair materials and bone void fillers is autologous cancellous bone. This type of bone has the advantage of being both osteoinductive and non-immunogenic. Unfortunately, autologous cancellous bone is not available under all circumstances. Moreover, donor site morbidity and trauma add to the limitations of autologous cancellous bone. One alternative to autologous bone is allograft bone. Unfortunately, allograft bone has a lower osteogenic capacity than autograft bone, has a high resorption rate, creates less revascularization at the bone defect site, typically induces a greater immunogenic response and may result in the transfer of certain diseases.

In order to avoid the disadvantages associated with the use of autologous and allograft bone, one may use synthetic bone materials in place of or in conjunction with natural bone material. However, known synthetic bone materials may suffer from one or more of the following drawbacks, including unacceptable workability, handling and setting parameters; insufficient density; undesirable absorption rates; and an inability to impart adequate stability.

For example, the use of some synthetic calcium salts, such as those formed into ceramic granules, in a bone void filler can cause the bone void filler to have poor handling characteristics but still facilitate bone growth at an implantation site. Further, while ceramic granules are used in various types of bone void fillers, often the ceramic granules are not uniform in size and porosity, and lack overall homogeneity. Such a lack of uniformity can cause problems with the stability of the bone void filler once implanted into the bone defect site and the bone void filler may undesirably migrate from the implant site.

Therefore, there is a need to provide a ceramic granule and a method of making a porous ceramic granule that can be tailored to have a specific size and porosity. There is also a need to provide a method of making a porous ceramic granule that has an increase in surface area that is ideal for bone growth and has better handling characteristics.

SUMMARY

Methods of making a porous ceramic granule are provided that can be tailored to have a specific size, porosity and microporosity that provide better handling characteristics when administered to a bone defect in a bone void filler.

In some embodiments, a method of making porous ceramic granules is provided. The method comprises heating pore-forming agent particles to a temperature above a glass transition temperature for the pore-forming agent particles; contacting the heated pore-forming agent particles with a ceramic material to form a mixture of pore-forming agent particles and ceramic material; heating the mixture to remove the pore-forming agent particles from the mixture to form a porous ceramic material; and micronizing the porous ceramic material to obtain the porous ceramic granules, wherein the porous ceramic granules have an average diameter from about 50 μm to 800 μm.

In some embodiments, porous ceramic granules are provided. The porous ceramic granules are made by the process of heating pore-forming agent particles to a temperature above a glass transition temperature for the pore-forming agent particles; contacting the heated pore-forming agent particles with a ceramic material to form a mixture of pore-forming agent particles and ceramic material; heating the mixture to remove the pore-forming agent particles from the mixture to form porous ceramic material; and micronizing the porous ceramic material to obtain the porous ceramic granules, wherein the porous ceramic granules have an average diameter from about 50 μm to 800 μm.

In some embodiments, a porous ceramic granule is provided. The porous ceramic granule comprises hydroxyapatite in an amount of about 8 to about 22 wt. % and beta-tricalcium phosphate in an amount of about 78 to about 92 wt. %. The porous ceramic granule has a microporosity and a diameter of each of the micropores is less than about 10 μm, a BET surface area from about 0.2 to about 10 m$^2$/g, and an average diameter from about 50 μm to 800 μm.

While multiple embodiments are disclosed, still other embodiments of the present application will become apparent to those skilled in the art from the following detailed description, which is to be read in connection with the accompanying drawings. As will be apparent, the present disclosure is capable of modifications in various obvious aspects, all without departing from the spirit and scope of the present disclosure. Accordingly, the detailed description is to be regarded as illustrative in nature and not restrictive.

BRIEF DESCRIPTION OF THE DRAWINGS

In part, other aspects, features, benefits and advantages of the embodiments will be apparent regarding the following description, appended claims and accompanying drawings.

FIG. 1 is a flow chart of the method of making the porous ceramic granules. The method comprises heating pore-forming agent particles to a temperature above a glass transition temperature for the pore-forming agent particles; contacting the heated pore-forming agent particles with a ceramic material to form a mixture of pore-forming agent particles and ceramic material; heating the mixture to remove the pore-forming agent particles from the mixture to form a porous ceramic material; and micronizing the porous ceramic material to obtain the porous ceramic granules, wherein the porous ceramic granules have an average diameter from about 50 μm to 800 μm.

It is to be understood that the figures are not drawn to scale. Further, the relation between objects in a figure may not be to scale and may in fact have a reverse relationship as to size. The figures are intended to bring understanding and clarity to the structure of each object shown, and thus, some features may be exaggerated in order to illustrate a specific feature of a structure.

DETAILED DESCRIPTION

Definitions

For the purposes of this specification and appended claims, unless otherwise indicated, all numbers expressing quantities of ingredients, percentages or proportions of materials, reaction conditions, and other numerical values used in the specification and claims, are to be understood as being modified in all instances by the term "about." Similarly, when values are expressed as approximations, by use of the antecedent "about," it will be understood that the particular value forms another embodiment that is +/−10% of the recited value. Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should at least be construed in light of the number of reported significant digits and by applying ordinary rounding techniques. Also, as used in the specification and including the appended claims, the singular forms "a," "an," and "the" include the plural, and reference to a particular numerical value includes at least that particular value, unless the context clearly dictates otherwise. Ranges may be expressed herein as from "about" or "approximately" one particular value and/or to "about" or "approximately" another particular value. When such a range is expressed, another embodiment includes from the one particular value and/or to the other particular value.

Notwithstanding that the numerical ranges and parameters setting forth the broad scope of this application are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

Biocompatible, as used herein, is intended to describe materials that, upon administration in vivo, do not induce undesirable long-term effects.

Bone, as used herein, refers to bone that is cortical, cancellous or cortico-cancellous of autogenous, allogenic, xenogenic, or transgenic origin.

Bone graft, as used herein, refers to any implant prepared in accordance with the embodiments described herein and therefore may include expressions such as a bone void filler.

The term "osteoinductive," as used herein, refers to the quality of being able to recruit cells from the host that have the potential to stimulate new bone formation. Any material that can induce the formation of ectopic bone in the soft tissue of an animal is considered osteoinductive.

The term "osteoinduction" refers to the ability to stimulate the proliferation and differentiation of pluripotent mesenchymal stem cells (MSCs). In endochondral bone formation, stem cells differentiate into chondroblasts and chondrocytes, laying down a cartilaginous ECM, which subsequently calcifies and is remodeled into lamellar bone. In intramembranous bone formation, the stem cells differentiate directly into osteoblasts, which form bone through direct mechanisms. Osteoinduction can be stimulated by osteogenic growth factors, although some ECM proteins can also drive progenitor cells toward the osteogenic phenotype.

The term "osteogenic" refers to the ability of a graft material to produce bone independently. To have direct osteogenic activity, the graft must contain cellular components that directly induce bone formation. For example, an allograft seeded with activated MSCs would have the potential to induce bone formation directly, without recruitment and activation of host MSC populations. Because many osteoconductive allografts also have the ability to bind and deliver bioactive molecules, their osteoinductive potential will be greatly enhanced.

The term "patient" refers to a biological system to which a treatment can be administered. A biological system can include, for example, an individual cell, a set of cells (e.g., a cell culture), an organ, or a tissue. Additionally, the term "patient" can refer to animals, including, without limitation, humans.

The term "implantable" as utilized herein refers to a biocompatible device (e.g., the composition) retaining potential for successful placement within a mammal. The expression "implantable composition" and expressions of the like import as utilized herein refers to an object implantable through surgery, injection, or other suitable means whose primary function is achieved either through its physical presence or mechanical properties. An example of the implantable device is the composition.

The term "thermoform" or "thermoforming" refers to the process where a material such as plastic is heated to a pliable forming or glass transition temperature to form a specific shape in a mold.

The "debind," or "debinding" refers to a process to remove a primary binding material from a mold. The mold can be created through a thermoforming process, as described above. Typically, there are multiple steps to the debinding process, and the part goes through more than one cycle to ensure as much of the binding material is removed as possible before sintering. After the debinding process, the part can be semi-porous, which can allow a secondary material to easily escape during a sintering cycle.

The term "amorphous" is defined a structure has no organization (not a crystalline structure), and the atomic structure resembles that of a liquid. Commonly, amorphous materials are amorphous solids unless otherwise clarified. Amorphous materials are characterized by atomic or molecular structures that are relatively complex and become ordered only with some difficultly. These materials are commonly prepared by rapidly cooling molten material. The cooling reduces the mobility of the material's molecules before they can pack into a more thermodynamic state.

The term "crystalline" is defined as a material that consists primarily of an organized crystal structure. A "crystal" is a solid composed of atoms, ions, or molecules arranged in a pattern that is repetitive in three-dimensions. Each crystal structure within a specific crystal system is defined by a unit cell. A unit cell is the smallest repeatable subsection of the crystal.

Method of Making Porous Ceramic Granules

Methods of making a porous ceramic granule are provided that can be tailored to have a specific size, porosity and microporosity that provide better handling characteristics when administered to a bone defect in a bone void filler.

As shown in FIGS. 1-10, a method of making porous ceramic granules is provided. The method allows the production of ceramic granules of a selected size, porosity, and microporosity that have a specific surface area that is beneficial for bone growth when administered to a bone defect as a bone graft such as, for example, a bone void filler.

Figure 1:
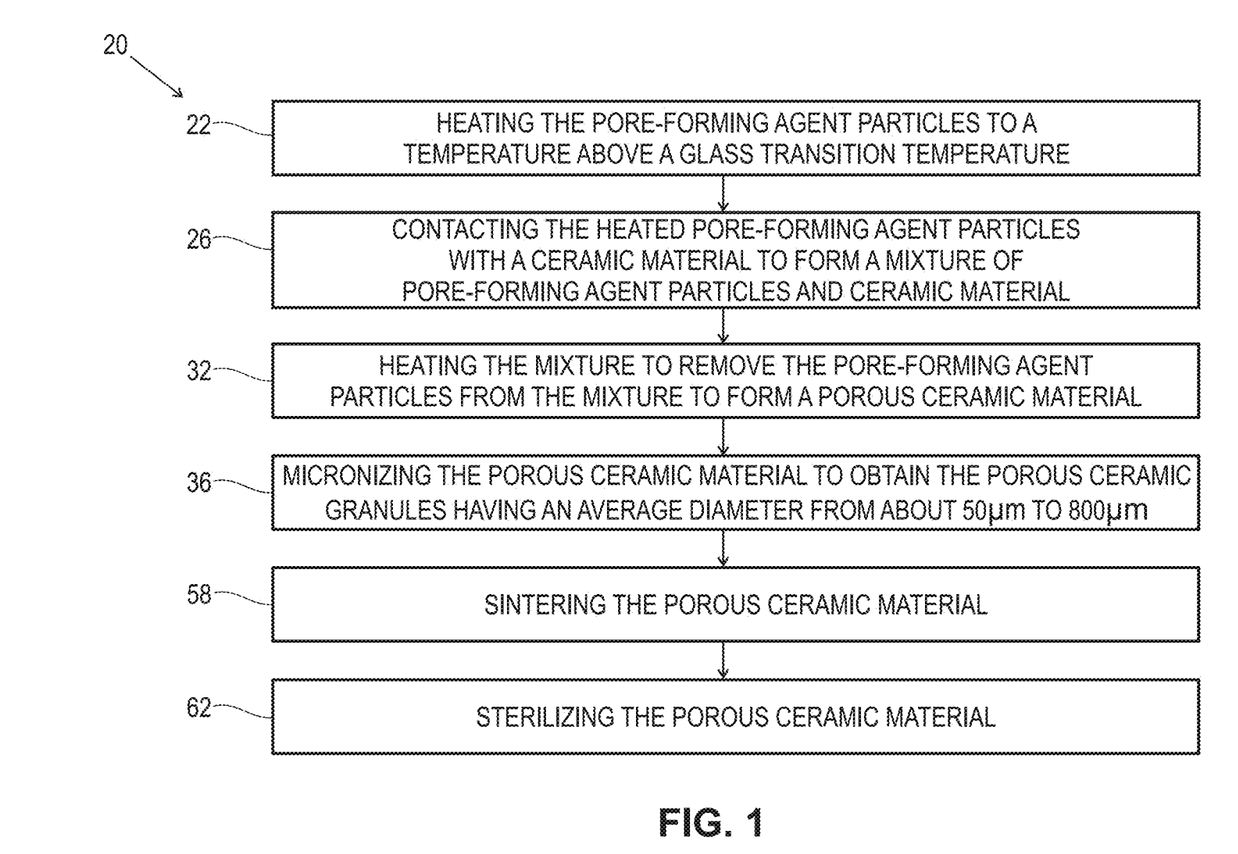

As shown in the flow chart of FIG. 1, the method 20 comprises heating 22 pore-forming agent particles 24 to a temperature above a glass transition temperature for the pore-forming agent particles; contacting 26 the heated pore-forming agent particles with a ceramic material 28 to form a mixture 30 of pore-forming agent particles and ceramic material; heating 32 the mixture to remove the pore-forming agent particles from the mixture to form a porous ceramic material 34; and micronizing 36 the porous ceramic material to obtain the porous ceramic granules 38, wherein the porous ceramic granules have an average diameter from about 50 μm to 800 μm.

The pore-forming agent particles can be polymeric, such as, for example, a thermoplastic polymer. Thermoplastic polymers can include, but are not limited to, polymethyl methacrylate (PMMA), polymethacrylate (PMA), polystyrene, polyethylene or a combination thereof. In some embodiments, the thermoplastic polymer selected is PMMA.

Figure 2:
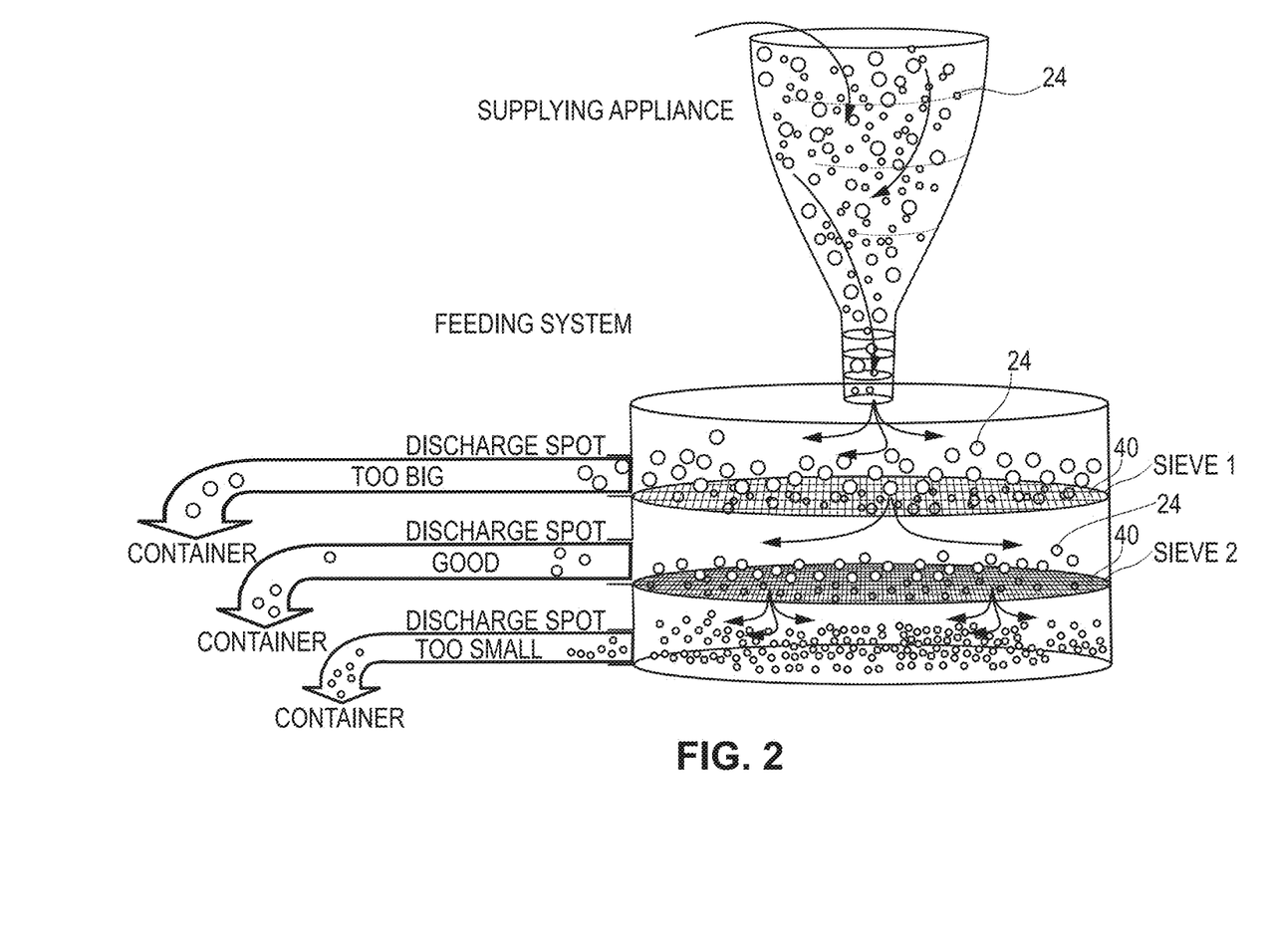
FIG. 2 is a front view of pore-forming agent particles such as polymethyl methacrylate (PMMA) that are fed through a plurality of sieves to calibrate the pore-forming particles to a selected size for use.

The pore-forming agent particles can be a specific size and each particle can have the same or different dimensions. It is contemplated that the particle size of the pore-forming agent particles can determine the macropore size as well as the microporosity of the final porous ceramic granules formed from the method. As shown in FIG. 2, a plurality of stacked sieves 40 having different pore or mesh sizes can be used to separate the pore-forming agent particles by size to obtain the selected size for use in the method.

For example, pore-forming agent particles that are selected for use would be particles having a size range of from about 40 to about 700 μm. The particles, in some embodiments, can be in a range from about 500 to about 670 μm, or from about 550 to about 600 m. The pore-forming agent particles can be from about 40, 50, 60, 70, 80, 90, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695 to about 700 μm.

The pore-forming agent particles can be an at least partially amorphous structure or a completely amorphous structure so as to avoid too great a volume increase during heat treatment. In some embodiments, the pore-forming agent particles are in the form of beads. Other shaped particles can be used including square, oval, irregularly shaped or a combination thereof.

The pore-forming agent particles are configured to degrade at a low temperature or a glass transition temperature such that the particles can coalesce to form a monobloc or interconnected porous structure for the ceramic material to interact with. For example, in the case of PMMA, the glass transition temperature is about 110° C. The pore-forming agent particles can degrade at a low temperature with only a small amount of residual impurities and of non-corrosive decomposition products. A thermoforming process can be used to heat the pore-forming agent particles.

As described above, the pore-forming agent particles are first heated to a temperature by a thermoforming process above a glass transition temperature for the selected pore-forming agent particles. For example, the temperature can be from 150 about to about 250° C. In some embodiments, the temperature can be from about 150° C. to about 180° C. The temperature can be from about 150, 155, 160, 165, 170, 175, 180, 185, 190, 195, 200, 205, 210, 215, 220, 225, 230, 235, 240, 245 to about 250° C. The particles can be heated for a period of time from about 14 to about 18 hours. The particles can be heated for a period time from about 14, 15, 16, 17 to about 18 hours.

Figure 3A:
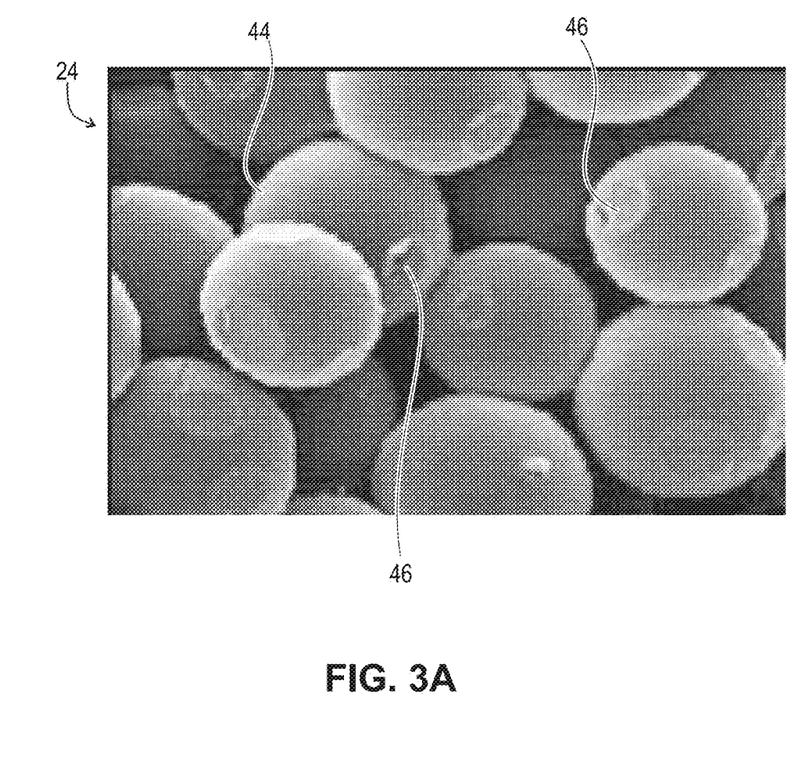
FIG. 3A is a SEM micrograph showing portions of the pore-forming agent particles that overlap diameters when the particles coalesce and interconnect.
Figure 3B:
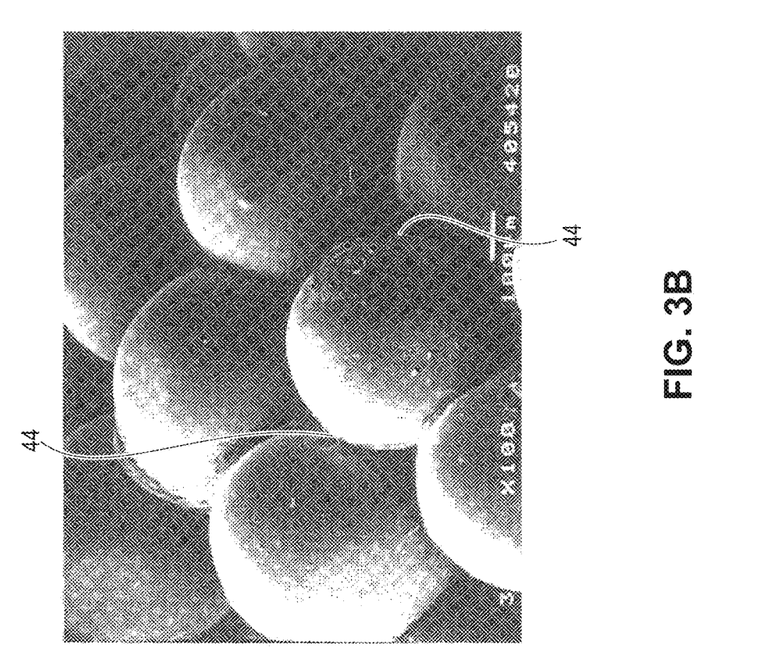
FIG. 3B is an SEM micrograph of a portion of an interconnected porous structure that is formed during heating of the pore-forming agent particles in a thermoforming process.

When the pore-forming agent particles are heated above their glass transition temperature, each of the particles contact one another and partially interlock to fuse the particles together. Once the heating step is completed, a monobloc or interconnected porous structure 42 is in a fixed state and contains pores or spaces 44 between the pore-forming agent particles, as shown in FIG. 3B. The pore-forming agent particles will contain overlapping diameters which can be visualized by a circle 46 on the exterior surface of each pore-forming agent particle, as shown in FIG. 3A. The circle indicates that an interconnection between beads has occurred and the circle is an interconnection rupture.

Prior to heating the pore-forming agent particles, the particles can be placed into a container that can withstand thermal degradation temperatures. The container can also be variously sized and shaped. Further, the container can be made from metal, plastic and/or aluminum. After the heating, the pore-forming agent particles now formed into the monobloc or interconnected porous structure can be placed into a new container or mold. The mold can be a porous mold.

Figure 6:
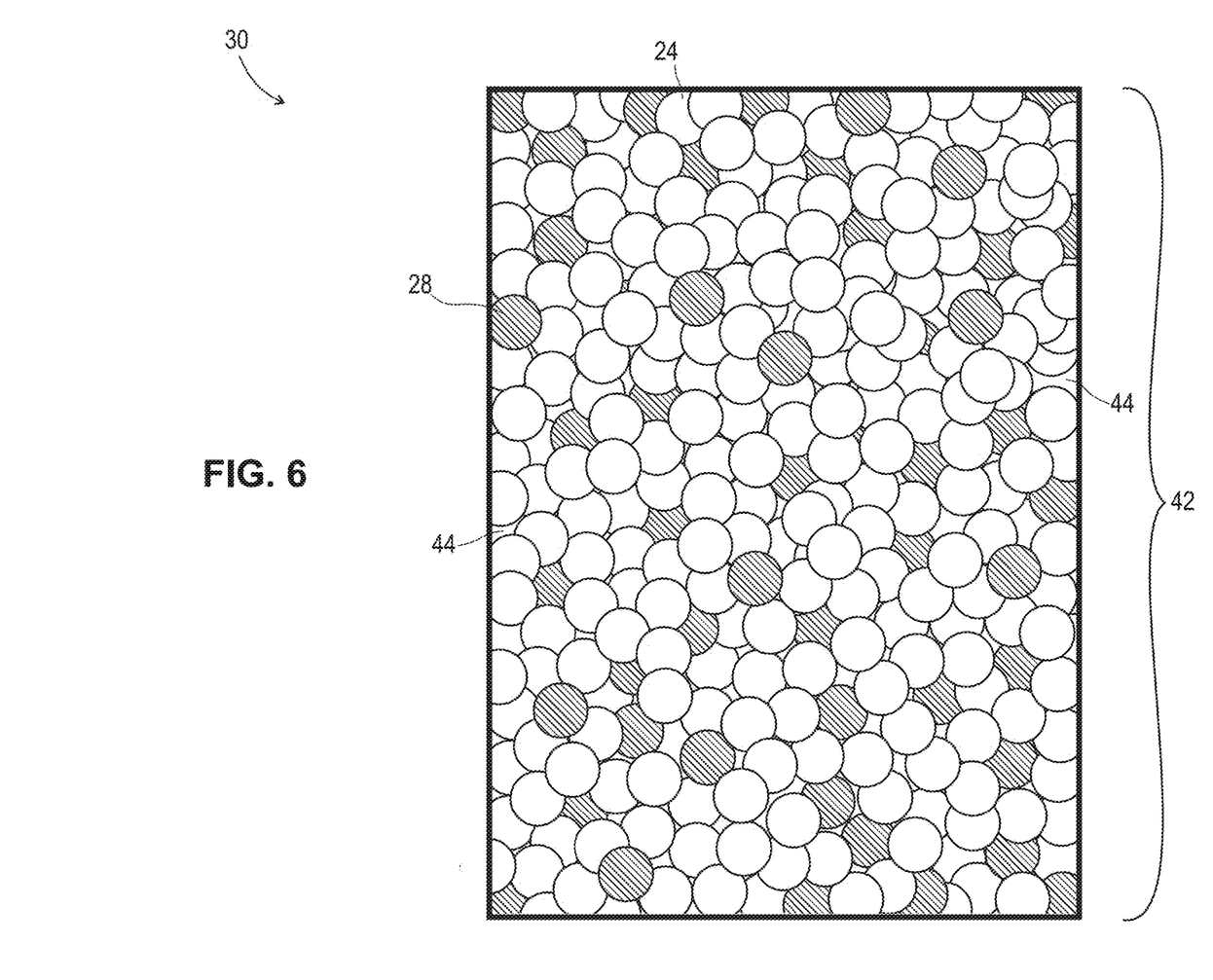
FIG. 6 illustrates a mixture of pore-forming agent particles and the ceramic material.

The next step is contacting the heated pore-forming agent particles with a ceramic material to form a mixture of pore-forming agent particles and ceramic material. In this step, the mixture of ceramic material fills in the pores or spaces created in between the pore-forming agent particles, as shown in FIG. 6. The mixture of ceramic material can be dispersed in a suspension or slurry 48. After contacting/adding the ceramic mixture to the pore-forming agent particles, the mixture can be air dried for a period of time such as, for about 3 hours, and can be further dried in a dryer for a period of time.

Figure 4:
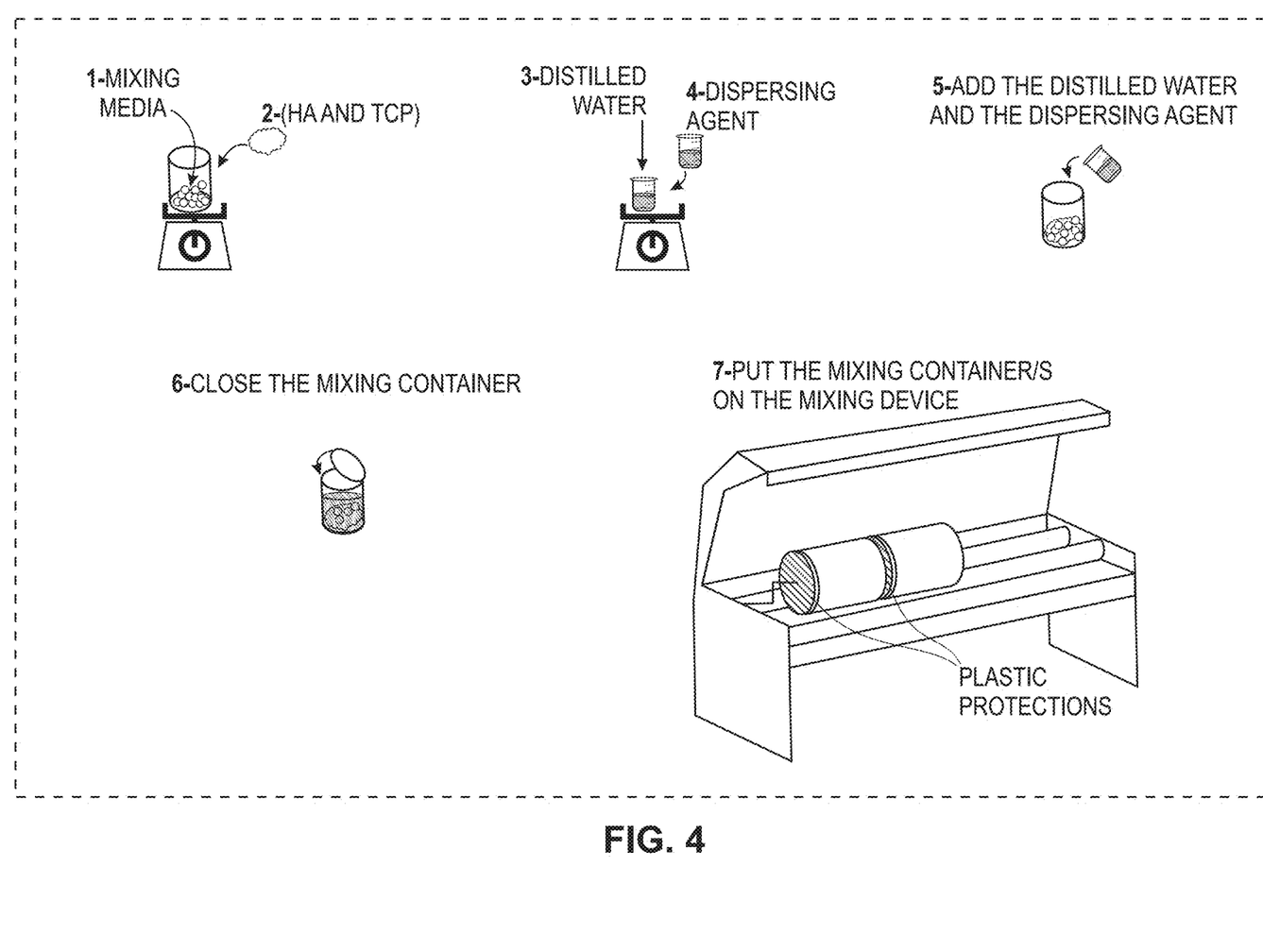
FIG. 4 illustrates the steps in making a ceramic material slurry that contacts the heated pore-forming agent particles to form a mixture of pore-forming agent particles and ceramic material. The ceramic material can be added to a mixing media to form a suspension or slurry.
Figure 5:
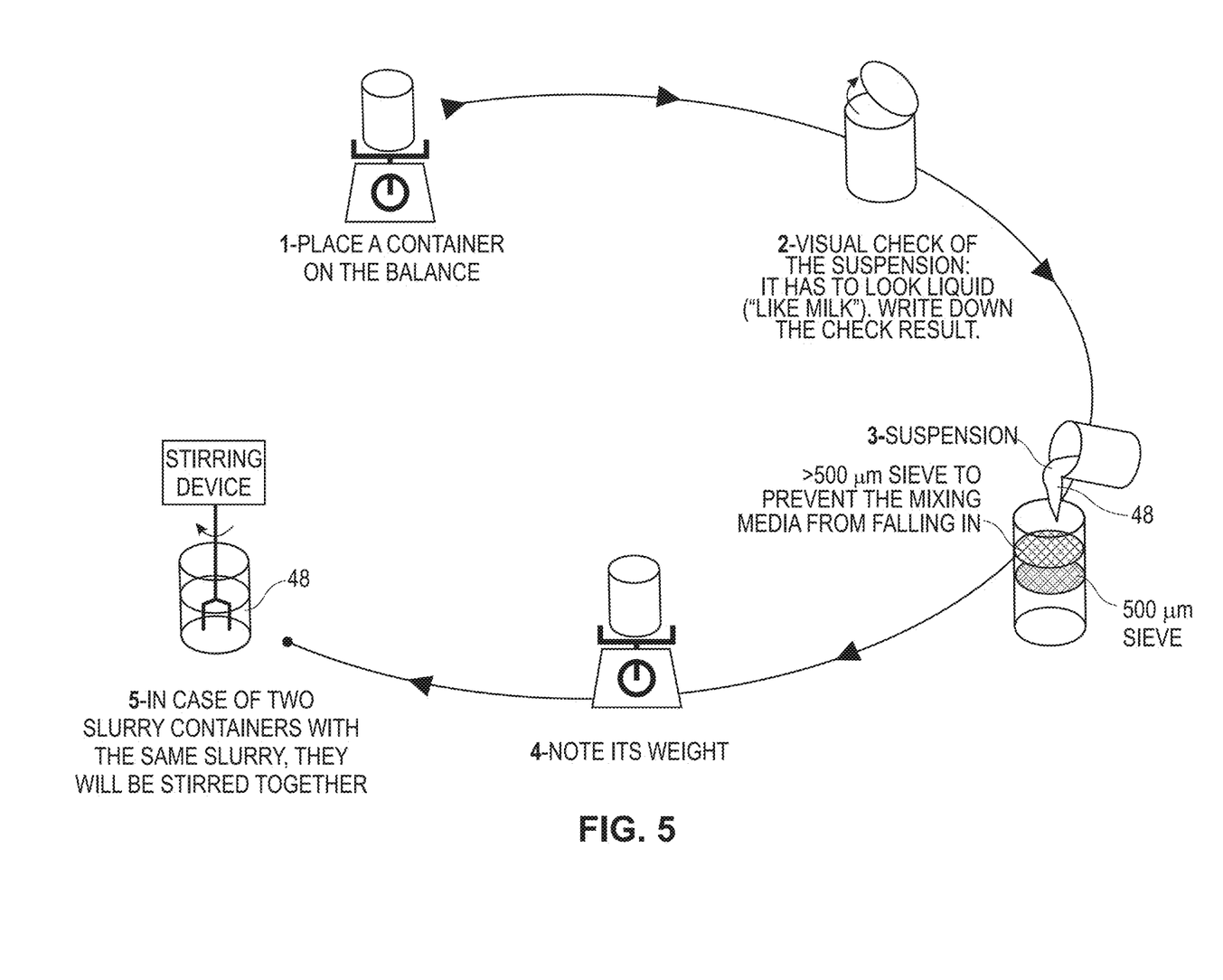
FIG. 5 illustrates the steps in making the ceramic slurry of FIG. 4 stirred before it contacts the heated pore-forming agent particles.

Before the ceramic material contacts with the heated pore-forming agent particles, the suspension or slurry of ceramic material is prepared. As shown in FIG. 4, the slurry or suspension can be made by adding the ceramic material to an amount of mixing media that is disposed in a container forming a mixture. An amount of distilled water and dispersing agent is then added to the mixture, and the container is closed. The container is then placed on a mixing device. As shown in FIG. 5, the container can then be placed on a balance to weigh the container with the mixture and can be visually inspected to see if the mixture has a "milk like" appearance. The mixture is then filtered through a sieve to remove the mixing media from the mixture. The resulting slurry or suspension is then placed into a second container. The weight of the container and slurry or suspension can be taken, and finally the container can be stirred with a stirring device (FIG. 5).

In some embodiments, the mixing media used to create the slurry or suspension can include materials such as, for example, sodium acetate buffer, sodium citrate buffer, sodium phosphate buffer, a Tris buffer (e.g., Tris-HCL), phosphate buffered saline (PBS), sodium phosphate, potassium phosphate, sodium chloride, potassium chloride, glycerol, calcium chloride or a combination thereof. In various embodiments, the buffer concentration can be from about 1 mM to 100 mM.

Exemplary organic solvents or non-aqueous solvents that can be in the mixing media include DMSO, acetic acid, acetone, DME, DMF, MTBE, acetonitrile, butanol, butanone, t-butyl alcohol, ethanol, polyethylene glycol, methanol, chlorobenzene, chloroform, toluene, propanol, pentane, heptane, ethanol, diethyl ether, or the like.

In some embodiments, the mixing media can include a binding agent to help the slurry or suspension retain its shape when contacting the heated pore-forming agent particles. Examples of suitable binding agents include, but are not limited to glycerol, polyglycerol, polyhydroxy compound, for example, such classes of compounds as the acyclic polyhydric alcohols, non-reducing sugars, sugar alcohols, sugar acids, monosaccharides, disaccharides, water-soluble or water dispersible oligosaccarides, polysaccarides and known derivatives of the foregoing. Specific polyhydroxy compounds include, 1,2-propanediol, glycerol, 1,4,-butylene glycol trimethylolethane, trimethylolpropane, erythritol, pentaerythritol, ethylene glycols, diethylene glycol, triethylene glycol, tetraethylene glycol, propylene glycol, dipropylene glycol; polyoxyethylene-polyoxypropylene copolymer, for example, of the type known and commercially available under the trade names Pluronic and Emkalyx; polyoxyethylene-polyoxypropylene block copolymer, for example, of the type known and commercially available under the trade name Poloxamer; alkylphenolhydroxypolyoxyethylene, for example, of the type known and commercially available under the trade name Triton, polyoxyalkylene glycols such as the polyethylene glycols, xylitol, sorbitol, mannitol, dulcitol, arabinose, xylose, ribose, adonitol, arabitol, inositol, fructose, galactose, glucose, mannose, sorbose, sucrose, maltose, lactose, maltitol, lactitol, stachyose, maltopentaose, cyclomaltohexaose, carrageenan, agar, dextran, alginic acid, guar gum, gum tragacanth, locust bean gum, gum arabic, xanthan gum, amylose, mixtures of any of the foregoing.

The ceramic material can comprise synthetic ceramic or ceramics including hydroxyapatite and beta-tricalcium phosphate. The ceramic material can be in a powder form. The ceramic material comprises a calcium to phosphate ratio of between 1.0 to about 2.0. In some embodiments, the calcium to phosphate ratio is between 1.0, 1.1, 1.2, 1.3, 1.4, 1.5, 1.6, 1.7, 1.8, 1.9 to about 2.0.

The ceramic material is a biphasic calcium phosphate comprising hydroxyapatite in an amount of about 8 to about 22 wt. % and beta-tricalcium phosphate in an amount of about 78 to about 92 wt. %. In some embodiments, the hydroxyapatite is in an amount of about 8, 9, 10, 11, 12, 13, 14, 15, 16, 17, 18, 19, 20, 21 to about 22 wt. % and the beta-tricalcium phosphate in an amount of about 78, 79, 80, 81, 82, 83, 84, 85, 86, 87, 88, 89, 90, 91 to about 92 wt. %.

The next step in the method is heating the mixture to remove the pore-forming agent particles from the mixture to form a porous ceramic material. This step can be considered a debinding or demolding step. In this step, heat is applied to the mixture to burn out the pore-forming agent particles, creating voids in the place of the pore-forming agent particles and leaving the porous ceramic material intact.

The mixture is heated at a temperature from about 200° C. to about 300° C. for a period of time and the heating can be done in an oven. The temperature can be from about 200, 205, 210, 215, 220, 225, 230, 235, 240, 245, 250, 255, 260, 265, 270, 275, 280, 285, 290, 295 to about 300° C. The heat treatment can be administered for a period of time from about 1 hour to about 20 hours. In some embodiments, the period of time is from about 1, 2, 3, 4, 5, 6, 7, 8, 9, 10, 11, 12, 13, 14, 15, 16, 17, 18, 19 to about 20 hours.

The next step in the method is micronizing the porous ceramic material to obtain the porous ceramic granules. The ceramic material can be granules that can be micronized and/or passed through a sieve to obtain the desired granule size. Micronization includes reducing the average diameter of porous ceramic granules. Typically, micronization includes using mechanical means to reduce the particle size of the porous ceramic granules, such as for example, by granulation, crushing, bashing, milling and/or grinding.

In some embodiments, a mill can be used to micronize the ceramic material, where the mill has a cylindrical drum that usually contains spheres. As the drum rotates the spheres inside collide with the ceramic material, thus crushing them towards smaller diameters. In some embodiments, with grinding, the ceramic granules can be formed when the grinding units of a device rub against each other while the granules are trapped in between them.

In some embodiments, methods like crushing and/or cutting may also be used for reducing particle size of the ceramic material. Crushing can employ, for example, hammer-like tools to break the porous ceramic into smaller particles by means of impact. In some embodiments, cutting can use sharp blades to cut the rough solid pieces into smaller ones. These micronization techniques can reduce the particle size of the ceramic to the micrometer size and these particles can be passed through one or more sieves by hand or machine to obtain the desired particle size of the porous ceramic granules. The resulting porous ceramic granules will have an average diameter from about 50 μm to 800 μm.

Figure 7:
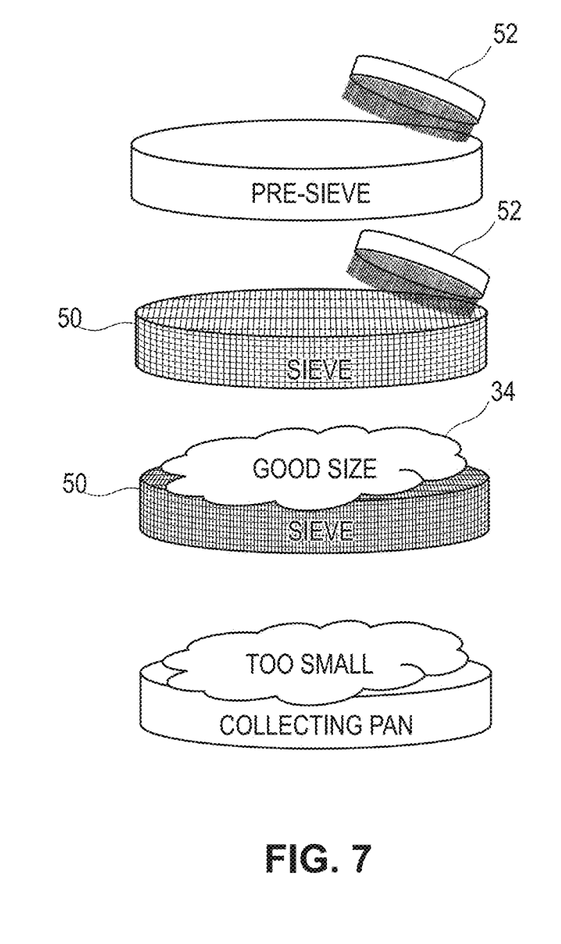
FIG. 7 illustrates the various sized sieves used to make micronized porous ceramic material that is formed after heating the mixture to remove the pore-forming agent particles from the mixture. The porous ceramic material is illustrated being micronized by passing the porous ceramic material through sieves of various sizes.
Figure 8:
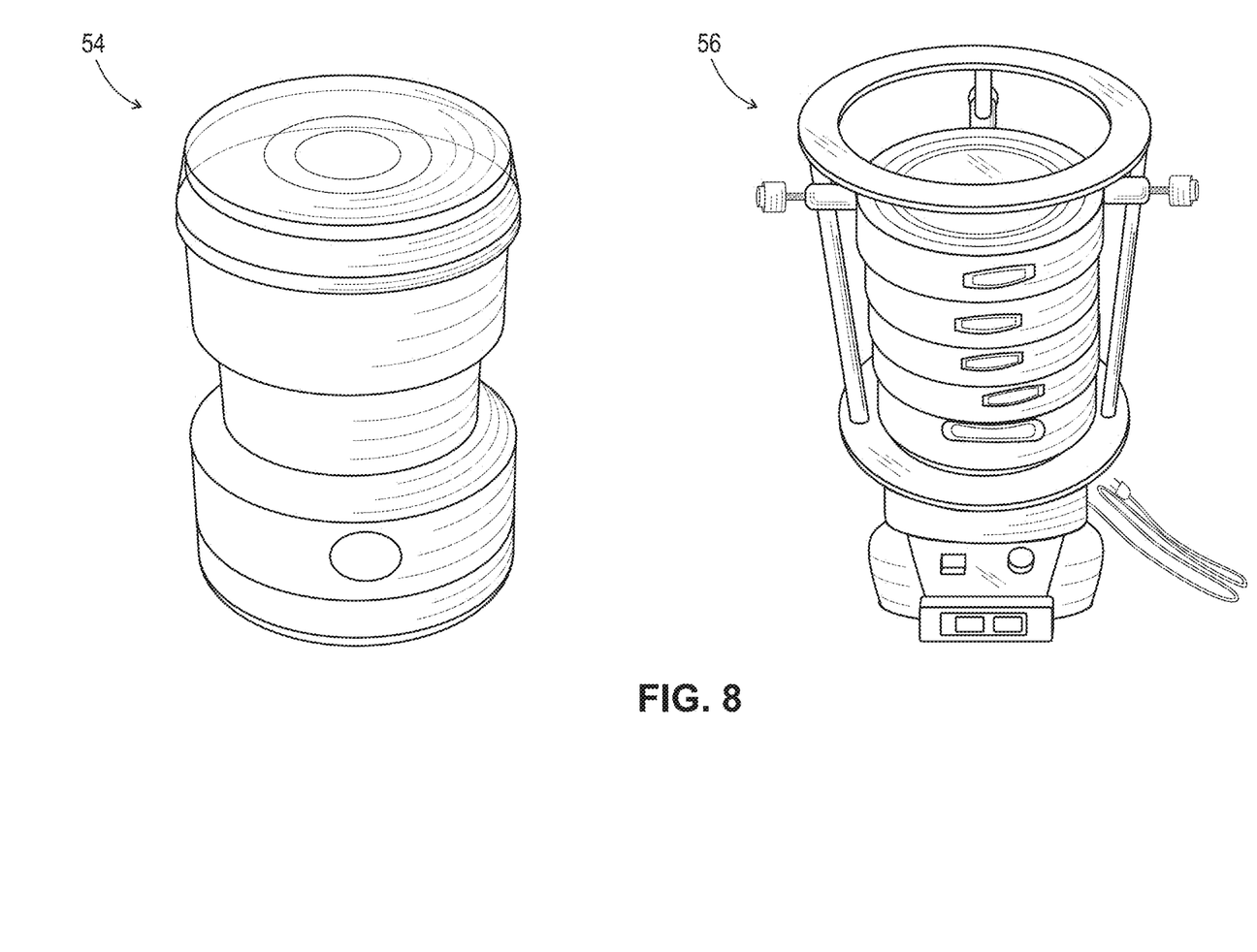
FIG. 8 is a perspective view of an automated crusher and an automated sieve that in some embodiments, are used to micronize the porous ceramic material.

In some embodiments, the ceramic material is micronized by passing the ceramic material through a sieve 50 using a crushing force, as shown in FIGS. 7 and 8. In some embodiments, the ceramic material is micronized by a manual crusher 52, such as a pin brush and a manual sieve, shown in FIG. 7. In some embodiments, the ceramic material is micronized by an automatic crusher 54 and an automatic sieve 56, shown in FIG. 8. A plurality of sieves may be used for micronizing the ceramic material, which enables the granules to be sorted out based on size, as shown in FIG. 7. For example, a sieve with a larger mesh pore size can be used first, followed by a subsequent sieve having a smaller mesh pore size. Each sieve used in a sequence can contain smaller mesh pore sizes than the previous sieve used. In some embodiments, the mesh pore sizes of each of the sieves can be from about 0.1 mm to about 4 mm. The mesh pore sizes of each of the sieves can be from about 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9 to about 4 mm.

As described above, after the micronizing step, the resulting porous ceramic granules having an average diameter from about 50 μm to 800 μm. In some embodiments, the average diameter of the granules is from about 90 μm to about 600 μm or from about 200 μm to about 500 μm. In some embodiments, the average diameter of the granules may be from about 50, 55, 60, 65, 70, 75, 80, 85, 90, 95, 100, 105, 110, 115, 120, 125, 130, 135, 140, 145, 150, 155, 160, 165, 170, 175, 180, 185, 190, 195, 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645, 650, 655, 660, 665, 670, 675, 680, 685, 690, 695, 700, 705, 710, 715, 720, 725, 730, 735, 740, 745, 750, 755, 760, 765, 770, 775, 780, 785, 790, 795 to about 800 μm.

After the micronizing step, in some embodiments, the porous ceramic granules can be optionally heated a second time to further debind the granules. This additional heat treatment can heat the porous ceramic granules at a temperature from about 200° C. to about 650° C. for a set period of time. The temperature can be from about 200, 205, 210, 215, 220, 225, 230, 235, 240, 245, 250, 255, 260, 265, 270, 275, 280, 285, 290, 295, 300, 305, 310, 315, 320, 325, 330, 335, 340, 345, 350, 355, 360, 365, 370, 375, 380, 385, 390, 395, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 605, 610, 615, 620, 625, 630, 635, 640, 645 to about 650° C. The heat treatment can be administered over a period of time, such as, from about 1 hour to about 5 hours. In some embodiments, the heat treatment is administered from about 1, 2, 3, 4 to about 5 hours.

A sintering step (58) can then be applied to the porous ceramic granules to increase the cohesion and rigidity of the granules, as shown in FIG. 1. The resulting granules are microporous with controlled interconnections and having an outer surface comprising a plurality of concave shapes, shown in FIG. 9 and as described herein.

The sintering step can occur in an oven at a temperature from about 1000° C. to about 1400° C. for a period of time. In some embodiments, the temperature is from about 1000, 1010, 1020, 1030, 1040, 1050, 1060, 1070, 1080, 1090, 1100, 1110, 1120, 1130, 1140, 1150, 1160, 1170, 1180, 1190, 1200, 1210, 1220, 1230, 1240, 1250, 1260, 1270, 1280, 1290, 1300, 1310, 1320, 1330, 1340, 1350, 1360, 1370, 1380, 1390 to about 1400° C. The sintering step can be administered for a period of time from about 1 to about 10 hours. In some embodiments, the period of time is from about 1, 2, 3, 4, 5, 6, 7, 8, 9 to about 10 hours.

Figure 10:
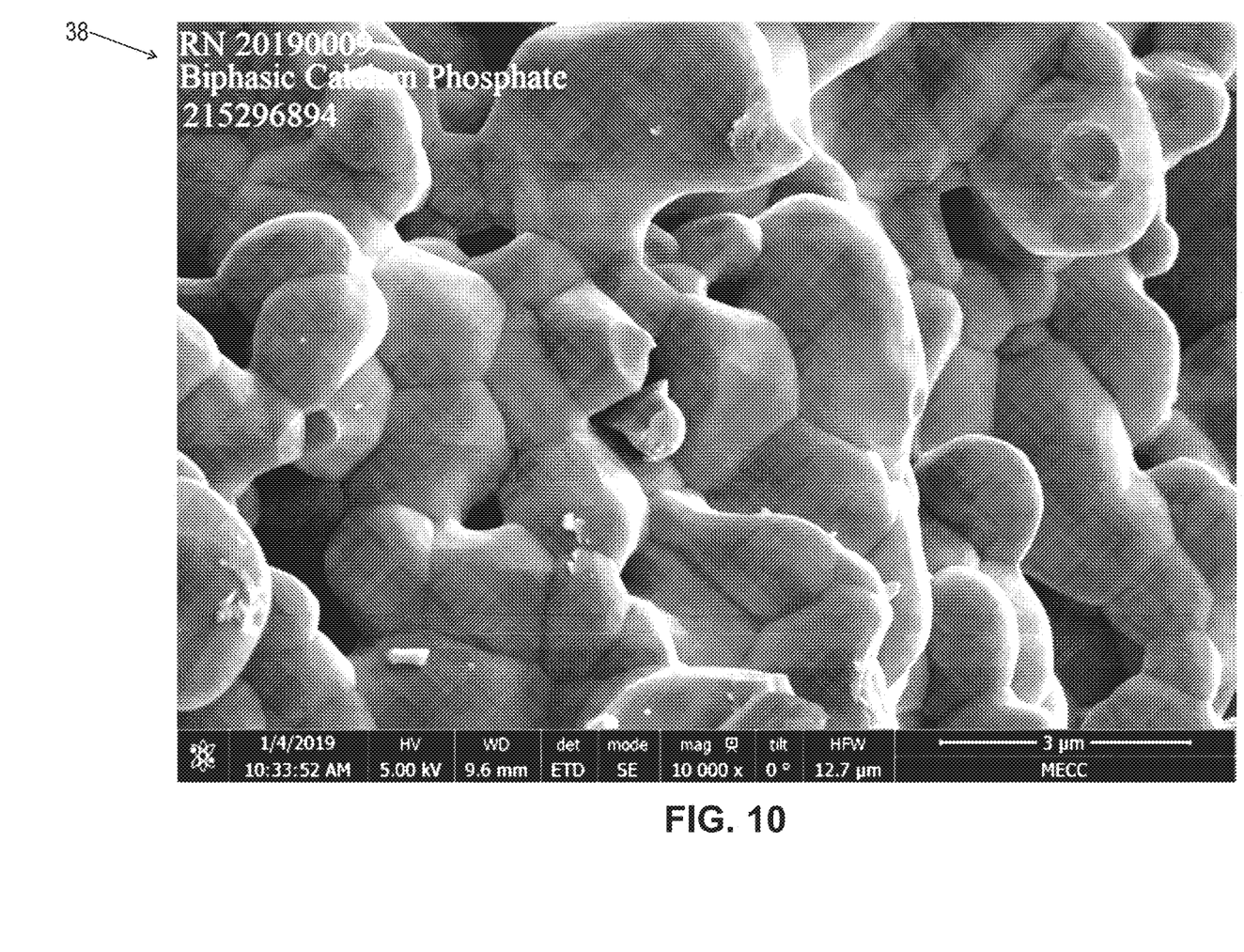
FIG. 10 is a SEM micrograph of the porous ceramic granules. As shown, the granules contain microporosity.

As described above, the porous ceramic granules each have a microporosity and the diameter of each of the micropores is from about 0.01 to about 10 microns, as shown in the SEM micrograph of FIG. 10. In some embodiments, the diameter of each of the micropores is from about 0.1 to about 10 microns or from about 1 to about 10 microns. In some embodiments, the diameter of each of the micropores can be from about 0.01, 0.02, 0.03, 0.04, 0.05, 0.06, 0.07, 0.08, 0.09, 0.1, 0.2, 0.3, 0.4, 0.5, 0.6, 0.7, 0.8, 0.9, 1, 2, 3, 4, 5, 6, 7, 8, 9 to about 10 microns. In some embodiments, the porous ceramic granules have a percent microporosity from about 10 to about 100% or from about 10, 20, 30, 40, 50, 60, 70, 80, 90 to about 100%.

Figure 9:
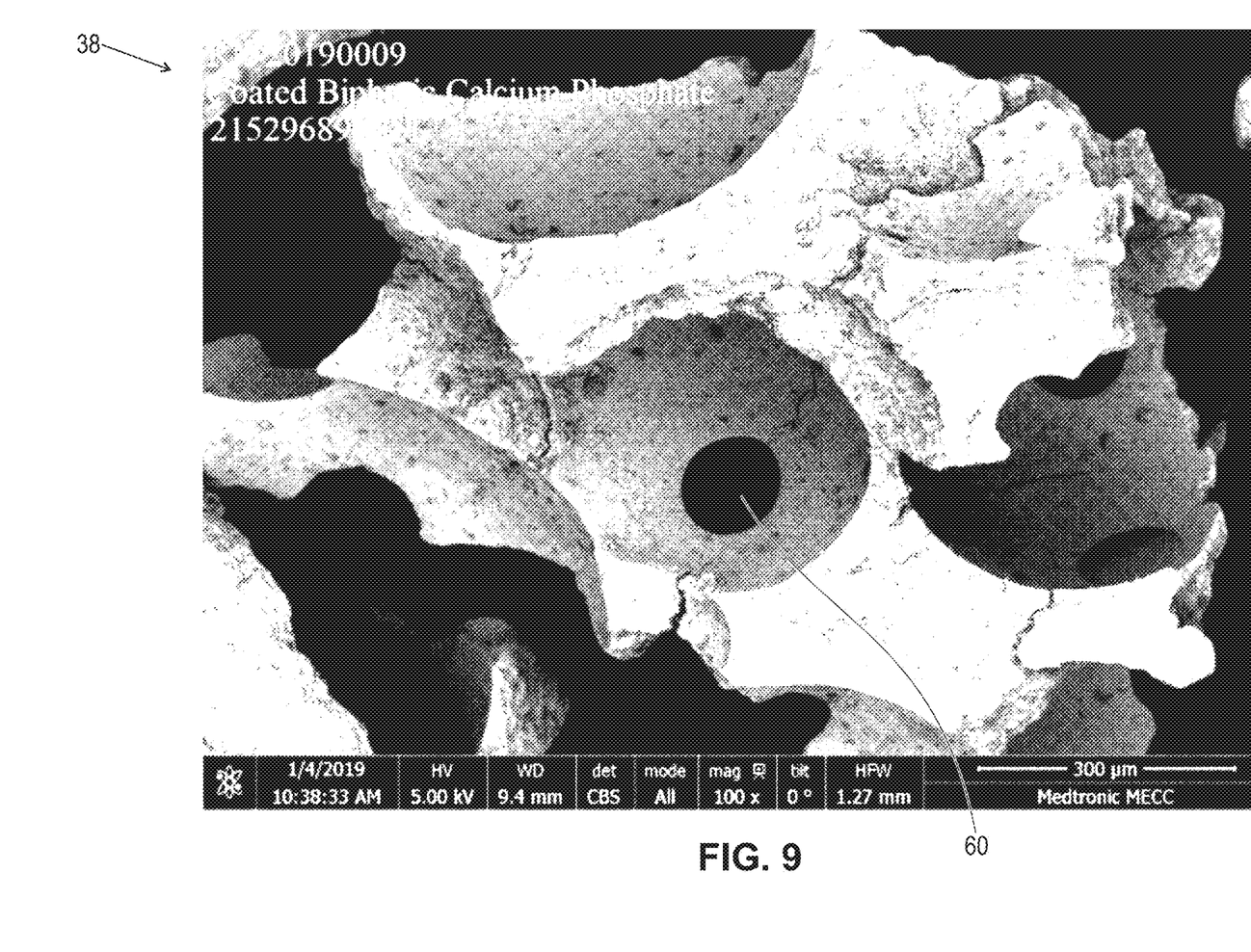
FIG. 9 is a SEM micrograph of the porous ceramic granules. The micrograph shows that the surface of the porous ceramic granules each have a concavity between 400 to about 600 microns.

The method described herein causes the porous ceramic granules to have an outer surface comprising a plurality of concave shapes 60, as shown in the SEM micrograph of FIG. 9. These concave surface features provide the granules with an irregular shape. The concave shapes can be disc like in appearance and can be a particular size. The concave shapes can each have a diameter from about 50 to about 1000 microns or from about 400 to about 600 microns. In some embodiments, each diameter can be from about 50, 75, 100, 125, 150, 175, 200, 225, 250, 275, 300, 325, 350, 375, 400, 405, 410, 415, 420, 425, 430, 435, 440, 445, 450, 455, 460, 465, 470, 475, 480, 485, 490, 495, 500, 505, 510, 515, 520, 525, 530, 535, 540, 545, 550, 555, 560, 565, 570, 575, 580, 585, 590, 595, 600, 625, 650, 675, 700, 725, 750, 775, 800, 825, 850, 875, 900, 925, 950, 975 to about 1000 microns. In some embodiments, the micronizing step is the step that causes the porous ceramic granules to have the concave shapes on the outer surface.

When disposed in a bone graft, the concave surfaces on the outer surface of each granule can facilitate an increase in new bone attachment since the surface makes new bone attachment easier (e.g., vascularization and penetration of associated cells) than attachment would be on a standard ceramic granule. In some embodiments, the porous ceramic granules facilitate rapid and homogeneous osseointegration which supports bone healing by acting as a scaffold over which bone can grow.

Each of the porous ceramic granules have a Brunauer-Emmett-Teller (BET) surface area from about 0.2 to about 10 m$^2$/g. The BET surface area can be from about 0.2, 0.3, 0.4, 0.5, 0.6, 0.7, 0.8, 0.9, 1, 2, 3, 4, 5, 6, 7, 8, 9 to about 10 m$^2$/g. The increase in surface area further facilitates new bone growth by allowing the granules to dissolve and release calcium faster than a regular granule would.

In some embodiments, the porous ceramic granules are in an amorphous form, a crystalline form or a combination thereof. When the porous ceramic granules are a combination of amorphous and crystalline, the granules can be from about 2 to about 98% amorphous to from about 98 to about 2% crystalline. When the granules are a combination of amorphous and crystalline, the granules can be from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 to about 98% amorphous and from about 2, 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, 68, 70, 72, 74, 76, 78, 80, 82, 84, 86, 88, 90, 92, 94, 96 to about 98% crystalline.

The method can also include a sterilization step (62), as shown in FIG. 1. In some embodiments, the porous ceramic granules can be sterilized by gamma radiation at a dose of about 25 kGy to about 40 kGy.

The porous ceramic granules can be packaged and stored for use. In various embodiments, the granules when packaged, can be sterilized by radiation in a terminal sterilization step. Terminal sterilization of a product provides greater assurance of sterility than from processes such as an aseptic process, which require individual product components to be sterilized separately and the final package assembled in a sterile environment.

In various embodiments, gamma radiation is used in the terminal sterilization step, which involves utilizing ionizing energy from gamma rays that penetrates deeply into the granules. Gamma rays are highly effective in killing microorganisms, they leave no residues nor have sufficient energy to impart radioactivity to the composition. Gamma rays can be employed when the granules are in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize the granules. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize the granules, including, but not limited to, gas sterilization, such as, for example, with ethylene oxide or steam sterilization.

In some embodiments, additional synthetic ceramics can be used to form the porous ceramic granules. The synthetic ceramics disclosed herein may be selected from one or more materials comprising calcium phosphate ceramics or silicon ceramics. Biological glasses such as calcium-silicate-based bioglass, silicon calcium phosphate, tricalcium phosphate (TCP), biphasic calcium phosphate, calcium sulfate, hydroxyapatite, coralline hydroxyapatite, silicon carbide, silicon nitride ($Si_3N_4$), and biocompatible ceramics may be used. In some embodiments, the ceramic is tri-calcium phosphate or biphasic calcium phosphate and silicon ceramics. In some embodiments, the ceramic is tricalcium phosphate.

In some embodiments, the ceramics are a combination of a calcium phosphate ceramic and a silicon ceramic. In some embodiments, the calcium phosphate ceramic is resorbable biphasic calcium phosphate (BCP) or resorbable tri-calcium phosphate (TCP).

In some embodiments, the biphasic calcium phosphate can have a tricalcium phosphate:hydroxyapatite weight ratio of about 50:50 to about 95:5, about 70:30 to about 95:5, about 80:20 to about 90:10, or about 85:15.

The ceramics of the disclosure may also be oxide ceramics such as alumina ($Al_2O_3$) or zirconia ($ZrO_2$) or composite combinations of oxides and non-oxides such as silicon nitride.

The porous ceramic granules can be used in a bone graft in any suitable application. For example, the granules can be administered in a bone graft which can be utilized in a wide variety of orthopedic, periodontal, neurosurgical, oral and maxillofacial surgical procedures such as the repair of simple and/or compound fractures and/or non-unions; external and/or internal fixations; joint reconstructions such as arthrodesis, general arthroplasty; cup arthroplasty of the hip; femoral and humeral head replacement; femoral head surface replacement and/or total joint replacement; repairs of the vertebral column including spinal fusion and internal fixation; tumor surgery, e.g., deficit filling; discectomy; laminectomy; excision of spinal cord tumors; anterior cervical and thoracic operations; repairs of spinal injuries; scoliosis, lordosis and kyphosis treatments; intermaxillary fixation of fractures; mentoplasty; temporomandibular joint replacement alveolar ridge augmentation and reconstruction; inlay implantable matrices; implant placement and revision; sinus lifts; cosmetic procedures; etc. Specific bones which can be repaired herein include the ethmoid, frontal, nasal, occipital, parietal, temporal, mandible, maxilla, zygomatic, cervical vertebra, thoracic vertebra, lumbar vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal and/or metatarsal bones.

In accordance with some embodiments, the granules may be treated or chemically modified with one or more bioactive agents or bioactive compounds. "Bioactive agent" or "bioactive compound," as used herein, refers to a compound or entity that alters, inhibits, activates, or otherwise affects biological or chemical events. For example, bioactive agents may include, but are not limited to, osteogenic or chondrogenic proteins or peptides; DBM powder; collagen, insoluble collagen derivatives, etc., and soluble solids and/or liquids dissolved therein; anti-AIDS substances, anti-cancer substances; antimicrobials and/or antibiotics such as erythromycin, bacitracin, neomycin, penicillin, polymycin B, tetracyclines, biomycin, chloromycetin, and streptomycins, cefazolin, ampicillin, azactam, tobramycin, clindamycin and gentamycin, etc.; immunosuppressants; anti-viral substances such as substances effective against hepatitis; enzyme inhibitors; hormones; neurotoxins; opioids; hypnotics; anti-histamines; lubricants; tranquilizers; anti-convulsants; muscle relaxants and anti-Parkinson substances; anti-spasmodics and muscle contractants including channel blockers; miotics and anti-cholinergics; anti-glaucoma compounds; anti-parasite and/or anti-protozoal compounds; modulators of cell-extracellular matrix interactions including cell growth inhibitors and antiadhesion molecules; vasodilating agents; inhibitors of DNA, RNA, or protein synthesis; anti-hypertensives; analgesics; anti-pyretics; steroidal and non-steroidal anti-inflammatory agents; anti-angiogenic factors; angiogenic factors and polymeric carriers containing such factors; anti-secretory factors; anticoagulants and/or antithrombotic agents; local anesthetics; ophthalmics; prostaglandins; anti-depressants; anti-psychotic substances; anti-emetics; imaging agents; biocidal/biostatic sugars such as dextran, glucose, etc.; amino acids; peptides; vitamins; inorganic elements; co-factors for protein synthesis; endocrine tissue or tissue fragments; synthesizers; enzymes such as alkaline phosphatase, collagenase, peptidases, oxidases, etc.; polymer cell scaffolds with parenchymal cells; collagen lattices; antigenic agents; cytoskeletal agents; cartilage fragments; living cells such as chondrocytes, bone marrow cells, mesenchymal stem cells; natural extracts, genetically engineered living cells or otherwise modified living cells; expanded or cultured cells; DNA delivered by plasmid, viral vectors, or other member; tissue transplants; autogenous tissues such as blood, serum, soft tissue, bone marrow, etc.; bioadhesives; bone morphogenic proteins (BMPs); osteoinductive factor (IFO); fibronectin (FN); endothelial cell growth factor (ECGF); vascular endothelial growth factor (VEGF); cementum attachment extracts (CAE); ketanserin; human growth hormone (HGH); animal growth hormones; epidermal growth factor (EGF); interleukins, e.g., interleukin-1 (IL-1), interleukin-2 (IL-2); human alpha thrombin; transforming growth factor (TGF-beta); insulin-like growth factors (IGF-1, IGF-2); parathyroid hormone (PTH); platelet derived growth factors (PDGF); fibroblast growth factors (FGF, BFGF, etc.); periodontal ligament chemotactic factor (PDLGF); enamel matrix proteins; growth and differentiation factors (GDF); hedgehog family of proteins; protein receptor molecules; small peptides derived from growth factors above; bone promoters; cytokines; somatotropin; bone digesters; antitumor agents; cellular attractants and attachment agents; immuno-suppressants; permeation enhancers, e.g., fatty acid esters such as laureate, myristate and stearate monoesters of polyethylene glycol, enamine derivatives, alpha-keto aldehydes, etc.; and nucleic acids.

In one embodiment, the granules can include osteoinductive agents comprising one or more members of the family of Bone Morphogenetic Proteins ("BMPs"). BMPs are a class of proteins thought to have osteoinductive or growth-promoting activities on endogenous bone tissue, or function as pro-collagen precursors. Known members of the BMP family include, but are not limited to, BMP-1, BMP-2, BMP-3, BMP-4, BMP-5, BMP-6, BMP-7, BMP-8, BMP-9, BMP-10, BMP-11, BMP-12, BMP-13, BMP-14 (GDF-5), BMP-15, BMP-16, BMP-17, BMP-18 as well as polynucleotides or polypeptides thereof, as well as mature polypeptides or polynucleotides encoding the same.

BMPs utilized as osteoinductive agents comprise one or more of BMP-1; BMP-2; BMP-3; BMP-4; BMP-5; BMP-6; BMP-7; BMP-8; BMP-9; BMP-10; BMP-11; BMP-12; BMP-13; BMP-15; BMP-16; BMP-17; or BMP-18; as well as any combination of one or more of these BMPs, including full length BMPs or fragments thereof, or combinations thereof, either as polypeptides or polynucleotides encoding the polypeptide fragments of all of the recited BMPs. The isolated BMP osteoinductive agents may be administered as polynucleotides, polypeptides, full length protein or combinations thereof.

Indeed, the osteoinductive factors are the recombinant human bone morphogenetic proteins (rhBMPs) because they are available in unlimited supply and do not transmit infectious diseases. In some embodiments, the bone morphogenetic protein is a rhBMP-2, rhBMP-4, rhBMP-7, or heterodimers thereof.

Recombinant BMP-2 can also be added to the granules. However, any bone morphogenetic protein is contemplated, including bone morphogenetic proteins designated as BMP-1 through BMP-18. BMPs are available from Pfizer, a Delaware corporation and the BMPs and genes encoding them may also be prepared by one skilled in the art as described in U.S. Pat. No. 5,187,076 to Wozney et al.; U.S. Pat. No. 5,366,875 to Wozney et al.; U.S. Pat. No. 4,877,864 to Wang et al.; U.S. Pat. No. 5,108,922 to Wang et al.; U.S. Pat. No. 5,116,738 to Wang et al.; U.S. Pat. No. 5,013,649 to Wang et al.; U.S. Pat. No. 5,106,748 to Wozney et al.; and PCT Patent Nos. WO93/00432 to Wozney et al.; WO94/26893 to Celeste et al.; and WO94/26892 to Celeste et al. All osteoinductive factors are contemplated whether obtained as above or isolated from bone. Methods for isolating bone morphogenetic protein from bone are described, for example, in U.S. Pat. No. 4,294,753 to Urist and Urist et al., 81 PNAS 371, 1984.

In addition to the above, the granules may include one or more members from the TGF-β superfamily. For example, the granules may include AMH, ARTN, GDF1, GDF10, GDF11, GDF15, GDF2, GDF3, GDF3A, GDF5, GDF6, GDF7, GDF8, GDF9, GDNF, INHA, INHBA, INHBB, INHBC, INHBE, LEFTY1, LEFTY2, MSTN, NODAL, NRTN, PSPN, TGFB1, TGFB2, TGFB3, FGF, basic FGF, VEGF, insulin-like growth factor, EGF, PDGF, nerve growth factor or combinations thereof.

In certain embodiments, the bioactive agent may be a drug. In some embodiments, the bioactive agent may be a small molecule, a growth factor, cytokine, extracellular matrix molecule, or a fragment or derivative thereof, for example, a protein or peptide sequence such as RGD.

Kits

In some embodiments, the porous ceramic granules may be packaged in a moisture resistant sterile package. In use, the porous ceramic granules can be added to a bone graft and administered to an orthopedic site.

In various embodiments, a kit is provided comprising the porous ceramic granules. The kit may include additional parts along with the granules combined together to be used to administer the bone graft (e.g., wipes, needles, syringes, mixing syringe or other mixing device, etc.). The kit may include the porous ceramic granules, or the porous ceramic granules already added to a bone graft in a first compartment. The second compartment may include the bone graft if the granules have not been added to the bone graft and any other instruments needed for the delivery. A third compartment may include gloves, drapes, wound dressings and other procedural supplies for maintaining sterility of the implanting process, as well as an instruction booklet, which may include a chart that shows how to administer the bone graft. A fourth compartment may include additional needles and/or sutures. Each tool may be separately packaged in a plastic pouch that is sterilized. A fifth compartment may include an agent for radiographic imaging. A cover of the kit may include illustrations of the implanting procedure and a clear plastic cover may be placed over the compartments to maintain sterility.

These and other aspects of the present application will be further appreciated upon consideration of the following Example, which is intended to illustrate a certain particular embodiment of the application but is not intended to limit its scope, as defined by the claims.

EXAMPLE

Example 1

Porous Ceramic Granules

Porous ceramic granules are made from the method described in the flowchart of FIG. 1 and described above. The porous ceramic granules have an average diameter from about 50 µm to 800 µm, comprise a biphasic calcium phosphate comprising hydroxyapatite in an amount of about 8 to about 22 wt. % and beta-tricalcium phosphate in an amount of about 78 to about 92 wt. %, have a microporosity and the diameter of each of the micropores is from about 0.1 to about 10 microns, comprise an outer surface comprising a plurality of concave shapes each having a diameter of from about 400 to about 600 microns and each of the porous ceramic granules have a BET surface area from about 0.2 to about 10 $m^2/g$.

Although the invention has been described with reference to preferred embodiments, persons skilled in the art will recognize that changes may be made in form and detail without departing from the spirit and scope of the invention.

What is claimed is:

1. Porous ceramic granules, the porous ceramic granules made by the process of heating pore-forming agent particles to a temperature above a glass transition temperature for the pore-forming agent particles having a size range of about 40 µm to about 700 µm; contacting the heated pore-forming agent particles with a ceramic material to form a mixture of pore-forming agent particles and ceramic material; heating the mixture to remove the pore-forming agent particles from the mixture to form porous ceramic material; and micronizing the porous ceramic material to obtain the porous ceramic granules, wherein the porous ceramic granules have an average diameter from about 50 μm to 800 μm, and each of the porous ceramic granules comprises micropores having a diameter from about 0.1 to about 10 microns and an interconnected porous structure and an outer surface comprising a plurality of concave shapes each having a diameter of about 400 to about 600 microns.

2. The porous ceramic granules of claim 1, wherein each of the porous ceramic granules have a Brunauer-Emmett-Teller (BET) surface area from about 0.2 to about 10 m$^2$/g.

3. A porous ceramic granule, the porous ceramic granule comprising hydroxyapatite in an amount of about 8 to about 22 wt. % and beta-tricalcium phosphate in an amount of about 78 to about 92 wt. %, the porous ceramic granule having a microporosity and each of the micropores have a diameter of less than about 10 μm, and a BET surface area from about 0.2 to about 10 m$^2$/g, and an average diameter from about 50 μm to 800 μm, the porous ceramic granules made by mixing the porous ceramic granules with pore-forming agent particles having a size range of about 40 μm to about 700 μm to form a mixture and heating the mixture to remove the pore-forming agent particles from the mixture to form the porous ceramic granules, wherein each of the porous ceramic granules comprises micropores having a diameter from about 0.1 to about 10 microns and an interconnected porous structure and an outer surface comprising a plurality of concave shapes, wherein each of the porous ceramic granules have a Brunauer-Emmett-Teller (BET) surface area from about 0.2 to about 10 m$^2$/g.

4. The porous ceramic granule of claim 3, wherein the porous ceramic granule is crystalline, amorphous or a combination thereof.

5. The porous ceramic granule of claim 3, wherein the porous ceramic granules comprise a calcium to phosphate ratio of between 1.0 to about 2.0.

6. A method of making the porous ceramic granules of claim 1, the method comprising heating pore-forming agent particles to a temperature above a glass transition temperature for the pore-forming agent particles, the pore-forming agent particles having a size range of about 40 μm to about 700 μm; contacting the heated pore-forming agent particles with a ceramic material to form a mixture of pore-forming agent particles and ceramic material; heating the mixture to remove the pore-forming agent particles from the mixture to form a porous ceramic material; and micronizing the porous ceramic material to obtain the porous ceramic granules of claim 1, wherein the porous ceramic granules have an average diameter from about 50 μm to 800 μm, and each of the porous ceramic granules comprises micropores having a diameter from about 0.1 to about 10 microns and an interconnected porous structure and an outer surface comprising a plurality of concave shapes each having a diameter of about 400 to about 600 microns.

7. The method of claim 6, wherein the porous ceramic granules have the average diameter from about 90 μm to about 600 μm.

8. The method of claim 6, wherein the porous ceramic granules have the average diameter from about 200 μm to about 500 μm.

9. The method of claim 6, wherein the pore-forming agent particles comprise polymethyl methacrylate (PMMA), polymethacrylate (PMA), polystyrene, polyethylene or a combination thereof.

10. The method of claim 6, wherein the pore-forming agent particles comprise polymethyl methacrylate (PMMA).

11. The method of claim 6, wherein heating the pore-forming agent particles to a temperature above a glass transition temperature for the pore-forming agent particles occurs in a thermoforming process.

12. The method of claim 11, wherein the thermoforming process occurs at a temperature from about 150° C. to about 180° C. for a period of time from about 14 to about 18 hours.

13. The method of claim 12, wherein the heated pore-forming agent particles during the thermoforming process creates the interconnected porous structure.

14. The method of claim 6, wherein heating the mixture to remove the pore-forming agent particles from the mixture to form the porous ceramic material is performed at a temperature from about 200° C. to about 300° C. for a period of time.

15. The method of claim 6, wherein the porous ceramic granules are micronized by passing the porous ceramic granules through a sieve using a crushing force.

16. The method of claim 6, wherein the ceramic material comprises hydroxyapatite and beta-tricalcium phosphate powder in a suspension or a slurry.

17. The method of claim 16, wherein the ceramic material comprises a calcium to phosphate ratio of between 1.0 to about 2.0.

18. The method of claim 6, wherein the ceramic material is a biphasic calcium phosphate comprising hydroxyapatite in an amount of about 8 to about 22 wt. % and beta-tricalcium phosphate in an amount of about 78 to about 92 wt. %.

\* \* \* \* \*